United States Patent [19]

Eilers et al.

[11] 4,385,910

[45] May 31, 1983

[54] APPARATUS AND METHOD FOR PRODUCING A GAS HAVING A CONTROLLED WATER VAPOR CONTENT

[75] Inventors: Melvin L. Eilers, Chillicothe; Michael S. Englund, Peoria, both of Ill.

[73] Assignee: Caterpillar Tractor Co., Peoria, Ill.

[21] Appl. No.: 334,009

[22] Filed: Dec. 23, 1981

[51] Int. Cl.³ .............................................. B01D 47/00
[52] U.S. Cl. .......................................... 55/90; 55/270; 55/259; 55/387; 55/267; 73/23; 73/1 G
[58] Field of Search ....................... 55/93, 95, 90, 158, 55/259, 270, 35, 84, 255, 256, 267; 73/23, 27 R, 1 G

[56] References Cited

U.S. PATENT DOCUMENTS

| | | | |
|---|---|---|---|
| 1,819,643 | 8/1931 | Fleisher | 55/35 |
| 3,735,558 | 5/1973 | Skarstrom et al. | 55/16 |
| 3,756,069 | 9/1973 | Carswell et al. | 73/27 R |
| 3,894,419 | 7/1975 | Mator et al. | 73/1 G |
| 3,895,915 | 7/1975 | Haldeman | 73/23 R |
| 3,976,450 | 8/1976 | Marcote et al. | 73/1 G |
| 4,049,402 | 9/1977 | Fortson | 55/257 R |
| 4,191,541 | 3/1980 | Jenkins | 55/270 |
| 4,269,057 | 5/1981 | Ong et al. | 73/1 G |

FOREIGN PATENT DOCUMENTS

587289 11/1959 Canada ................................. 55/270
286020 2/1965 Netherlands ....................... 73/23 R

OTHER PUBLICATIONS

*Chemiluminescent Measurement of Nitric Oxide in Combustion Products*, by Blair A. Folsom and Craig W. Courtney, Feb. 1979 at Proceeding of the Third Stationary Source Combustion Symposium; vol. II, Advanced Processes and Special Topics; EPA, Office of Research and Development.

*Primary Examiner*—Bernard Nozick
*Attorney, Agent, or Firm*—Robert A. McFall

[57] ABSTRACT

An apparatus (10) and method for producing a gas having a controlled water vapor content is disclosed. Present methods of adding varying amounts of water to a gas containing nitric oxide may undesirably alter the composition of the gas.

The present invention solves the above problem by providing an apparatus (10) and method for substantially fully saturating an unconditioned gas, subsequently removing water from a preselected portion of the saturated gas, and then mixing the preselected dry and saturated portions of the gas.

The present invention is particularly useful in calibrating exhaust emission analyzers.

7 Claims, 1 Drawing Figure

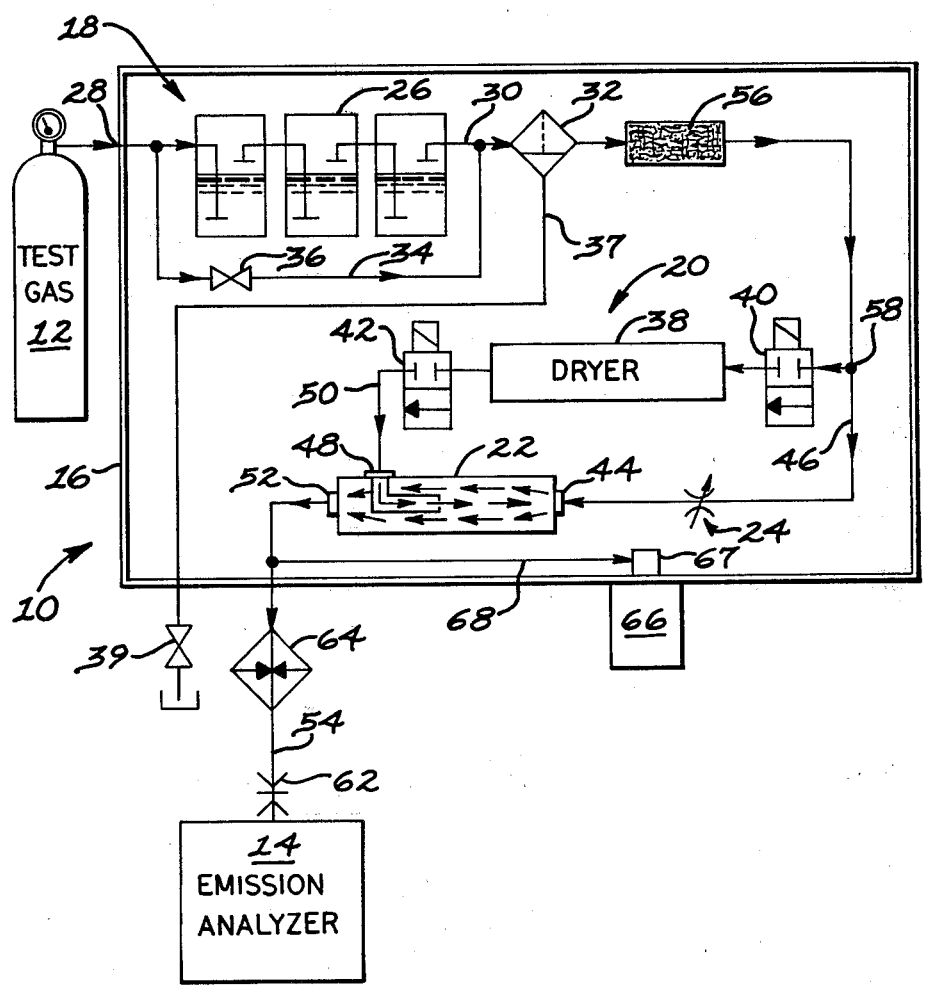

APPARATUS AND METHOD FOR PRODUCING A GAS HAVING A CONTROLLED WATER VAPOR CONTENT

TECHNICAL FIELD

This invention relates generally to an apparatus and method for producing a gas having a controlled water vapor content and more particularly to an apparatus and method for producing such a gas by saturating an unconditioned gas and subsequently removing water vapor from a preselected portion of the saturated gas.

BACKGROUND ART

It is becoming increasingly necessary to accurately measure gas compositions and in particular to accurately measure transient engine exhaust emissions. Exhaust gas emissions are generally measured by either a chemiluminescent or a non-dispersive infrared analyzer. The amount of water vapor in an exhaust gas sample can be a significant source of error affecting the measurement of engine exhaust emissions by both types of analyzers. Diesel engine exhaust gas, for example, may contain as much as 15% water vapor by volume. If an atmospheric chamber chemiluminescent analyzer is used to measure nitric oxide (NO) in diesel engine exhaust gas, water vapor will negatively affect the operation of the analyzer and, for a wet exhaust gas sample containing 15% water vapor, the indicated amount of NO may be as much as 30% below the actual amount present in the sample. In contrast, water vapor in the exhaust gas will positively influence the analysis mechanism in an uncompensated non-dispersive infrared analyzer resulting in an indicated NO measurement higher than the actual amount of NO present in the sample.

In response to the above problem, a number of attempts have been made to establish correction factors for specific analyzers and gas samples having a known water vapor content. One approach has been to pass a dry gas of a known composition through a conventional water bubbler. In this method, the bubbler temperature, partial pressure, number of stages, and gas flow rate are varied to produce a desired saturation level in the gas. However, in passing gas compositions containing nitric oxide (NO) through a water bubbler, some of the NO may convert to $NO_2$ and combine with the water in the bubbler. Further, the amount of loss of NO from the test gas varies with the flow rate and saturation level of the gas. The composition of the resultant gas is thereby undesirably altered, negating the establishment of a predetermined correction factor.

In a second method for controlling the water vapor content of a gas containing $NO_2$ or other water-reactive components, a non-reactive carrier gas such as nitrogen or argon is saturated by passing through one or more water bubbler stages and then combined with the test gas. This method is described in a report titled *Chemiluminescent Measurement of Nitric Oxide in Combustion Products* by Blair A. Folsom and Craig W. Courteney, presented March, 1979 at the Third Stationary Source Combustion Symposium sponsored by the EPA Office of Research and Development. This method, while being effective in preventing dilution of NO in the test gas, has the inherent disadvantage of a limited saturation level in that only a portion of the resultant gas passes through the bubbler stages.

A less conventional approach has been to reactively combine hydrogen and oxygen to form water in the test gas. However, this method is not compatible with all gas compositions.

The present invention is directed to overcoming one or more of the problems as set forth above. More particularly, the present invention provides both an apparatus and a method for controllably saturating a gas without undesirably altering the composition of the gas.

DISCLOSURE OF THE INVENTION

In accordance with one aspect of the invention, an apparatus for producing a gas having a controlled water vapor content includes a first means for adding water vapor and forming a first mixture, a second means for removing water vapor from at least a portion of the first mixture and forming a second mixture, and a valve for delivering preselected amounts of the first and second mixtures to a mixing chamber. The first and second means and the mixing chamber are positioned within an oven.

In another aspect of the present invention, a method for controlling the water vapor content of a gas includes adding water vapor to an unconditioned gas in an amount sufficient to raise the saturation of the gas to a range of about 95% to 99% and forming a first mixture, and removing water vapor from a preselected portion of the first mixture to form a second mixture. A resultant third mixture is formed by mixing preselected portions of the first and second mixtures.

The presence of water vapor in internal combustion exhaust gases adversely influences the analysis of such gas compositions for nitric oxide. Present methods of adding water vapor to sample gas compositions may produce undesirable changes in the composition of the gas and thereby provide additional sources for error when using such gases to calibrate test instruments.

The present invention overcomes the above problems by providing an apparatus and method for controllably introducing water vapor to a test gas sample without adversely changing the composition of the gas as a function of the saturation level. The present invention is particularly useful in calibrating exhaust emission analyzers and in determining appropriate correction factors to apply to measurements by such instruments of exhaust gases having a known water vapor content.

BRIEF DESCRIPTION OF THE DRAWINGS

The single FIGURE of the drawing is a schematic view of an embodiment of the present invention.

BEST MODE FOR CARRYING OUT THE INVENTION

An apparatus for producing a gas having a controlled water vapor content is generally indicated in the schematic drawing by the reference numeral 10. The apparatus 10 is shown in conjunction with a supply of a dry, unconditioned test, or span, gas 12 of a known composition, and a conventional gaseous emission analyzer 14. A typical test gas composition for use in calibrating the emission analyzer 14 comprises approximately 1000 ppm nitric oxide (NO), 3 ppm nitrogen dioxide ($NO_2$), and the balance diatomic nitrogen ($N_2$).

The apparatus 10 includes a thermostatically controlled oven 16, a first means 18, disposed inside the oven 16, for adding water vapor to the test gas 12 and forming a first mixture, and a second means 20, also disposed within the oven 16, for removing water vapor from at least a portion of the first mixture and forming a second mixture. The apparatus 10 also includes a mixing chamber 22 disposed inside the oven 16 and operatively connected, as will be subsequently described in more detail, to the first means 18 and the second means 20. Also included in the apparatus 10 is a valve means 24 for selectively, controllably delivering preselected amounts of the first and second mixtures to the mixing chamber 22 and forming a third resultant mixture.

The first means 18 for adding water vapor to the unconditioned gas 12, preferably includes a three-stage water bubbler 26 of conventional construction. The first stage of the water bubbler 26 is connected to one end of a conduit 28, the opposite end of the conduit 28 being connected to a discharge port of the gas supply 12.

A conduit 30 is connected between the third stage of the water bubbler 26 and a water trap 32, placing the bubbler 26 in fluid communication with the trap 32. A bypass conduit 34 extends between the conduit 28 and the conduit 30 and includes a valve 36 for selectively directing a flow of gas directly from the gas supply 12 to the water trap 32. In normal operation, the valve 36 is closed and all of the unconditioned gas 12 is passed through all three stages of the water bubbler 26, forming a saturated first mixture.

The water trap 32 has a drain line 37 extending externally of the oven 16 and a valve 39 positioned in the drain line 37 to selectively drain condensed water from the trap 32.

The second means 20 for removing water vapor from at least a portion of the first mixture preferably includes a standard permeation distillation dryer 38. The permeation distillation dryer 38 has a plurality of thin wall tubes formed of an extrudable desiccant material and disposed within an impermeable shell. One such dryer that has been found to be particularly effective is a model PD-1000-12S multi-tube dryer manufactured by Perma Pure Products, Inc. of Oceanport, N.J., U.S.A. The dryer 38 has a solenoid-operated normally-closed inlet valve 40 positioned at a gas inlet end and a similar solenoid-operated normally-closed outlet valve 42 at a gas outlet end respectively of the dryer 38. Water vapor is removed from the preselected portion of the saturated first mixture gas passing through the dryer 38 and a substantially dry second mixture of gas is discharged from the dryer 38 through the outlet valve 42.

The mixing chamber 22 is preferably a cylindrical chamber having a first inlet port 44 in communication with the first means 18 by way of a conduit 46, a second inlet port 48 in communication with the second means 20 by way of a conduit 50, and a discharge port 52 in communication with the emission analyzer 14 by way of a conditioned gas discharge conduit 54. A tube 56 is internally disposed within the mixing chamber 22 and provides a flow path between the second inlet port 48 and the internal cavity of the chamber 22. Desirably, as an aid to mixing, gas introduced into the chamber 22 through the second inlet port 48 is directed by the tube 56 in a flow direction counter to the flow direction of gas introduced through the first inlet port 44.

A filter 56, preferably having an element sized to trap particles greater than 10 micron, is preferably disposed, in series, with the conduit 46 to filter the first mixture of gas after the first mixture is discharged from the water trap 32. The conduit 46 also has a tee connection 58 to the inlet valve 40 of the dryer 38.

The valve means 24 for selectively and controllably delivering preselected amounts of the first and second mixtures to the mixing chamber 22 is preferably a variable throttle valve disposed in series with the conduit 46 at a position intermediate to the tee-connection 58 and the first inlet port 44 of the mixing chamber 22.

Modulation of the valve means 24 will controllably alter the relative amounts of the saturated first mixture directed through dryer 38 and the mixing chamber 22. Water vapor is removed from the preselected portion of the saturated first mixture directed through the dryer 38 of the second means 20 forming a substantially dry second mixture. The second mixture is discharged from the dryer 38 of the second means 22 through the outlet valve 42, and the conduit 50 to the second inlet port 48 and hence into the mixing chamber 22. The remaining portion of the saturated first mixture is directed by the valve means 24 directly to the first inlet port 44 and hence into the mixing chamber 22 whereupon the first and second mixtures are combined, forming a resultant third mixture having a preselected water vapor content.

The apparatus 10 also includes a coupling member 62 attached to an end of the conditioned gas discharge conduit 54 at a position spaced from the oven 16. Preferably the coupling member 62 is a quick-disconnect type fitting adapted to mate with a fitting provided on the emission analyzer 14. It is also desirable that the conditioned gas discharge conduit 54 have a heating means 64 for maintaining the conduit 54 at a temperature above the dew point temperature of a gas passing through the conduit 54. One such heating means includes a tape-type resistance heater wrapped about the line and a layer of insulation placed over the tape and conduit. The apparatus 10 also preferably includes a dew point measuring instrument 66 having a sensing head 67 disposed within the oven 16, the sensing head 67 being in fluid communication with the conditioned gas discharge conduit 54 by way of a conduit 68.

INDUSTRIAL APPLICABILITY

Emission analyzer vapor interference is defined as the difference between the correct response and the observed divided by the correct response; i.e., $$\% \text{ interference} = [R_c - R_o] \times 100 R_c \qquad (1)$$

where $R_o$ is the observed response and $R_c$ is the correct or predicted response.

$R_c$ also equals:

$$R_c = (\text{NO concentration in dry test gas}) \times (1 - \% H_2O) \qquad (2)$$

If the test gas supply 12 contains $NO_2$ molecules, as is typically found in actual practice, or if the NO in the test gas supply 12 reacts with oxygen prior to reaching the bubbler 26, a portion of the $NO_2$ will be trapped in the water bubbler 26 as nitric acid and the amount of NO measured by the emission analyzer 14 will be less than the original concentration in the dry gas sample. Although this error is distinct from the error resulting from the presence of water vapor in the measured sample, it has heretofore been difficult to separate the two sources of error. The present invention solves this problem by passing all of the test gas through the bubbler 26 and removing varying amounts of water vapor from the saturated gas prior to measurement by the analyzer 14.

To place the apparatus 10 in operation, the water bubbler is filled with distilled water to an appropriate level, typically about one-half capacity, and the oven temperature is stabilized at a predetermined temperature, which preferably is about 160° F. (71° C.). It is desirable to heat the unconditioned gas to a temperature in a range from about 40° C. (140° F.) to about 75° C. (168° F.) and maintain said first and second mixtures at the same temperature range. In addition, ancillary support equipment, not shown, such as auxiliary cooling for the dew point measuring instrument 66 and purge gas flow for the dryer 38, is activated. The heating means 64 for the conditioned gas discharge conduit 54 is also activated and thermally stabilized at a temperature sufficiently near the oven temperature to prevent the undesirable condensation of wet gas samples passing to the analyzer 14.

The analyzer 14 is initially calibrated by passing a flow of dry test gas to the analyzer 14. During this initial operation, the valve 36 in the bypass conduit 34 is opened and a flow of gas is directed from the gas supply 12, through the conduit 34 and trap 32, to the conduit 46. The inlet valve 40 and the outlet valve 42 of the dryer 38 are in the normally-closed position and the valve means 24 is open to direct the gas flow to the first inlet port 44 of the mixing chamber 22. At this time there is no flow of gas from the dryer 38, and the gas passing into the mixing chamber 22 continues, without mixing, through the chamber 22, the discharge port 52 and the conduit 54, to the emission analyzer 14. The analyzer 14 can now be initially calibrated based on the known composition of gas supply 12.

After the above initial calibration, the valve 36 in the bypass conduit 34 is completely closed and all of the flow from the gas supply 12 is directed through all three stages of the water bubbler 26. Since typical exhaust gases from an internal combustion engine may contain as much as 15% water by volume, it is desirable to know the influence that amount of water will have on the observed reading of the analyzer 14. In order to achieve the desired 15% water by volume, the oven 16, the bubbler 26, and the gas must be heated to at least about 131° F. (55° C.).

A 100% saturation level is undesirable in that small changes in system temperatures downstream of the bubbler 16 may condense water from the saturated gas stream.

It is therefore desirable that the bubbler force the dry gas to between 95% and 99% saturation. For the above reason, a 97% saturation level is preferred. To provide a gas sample at a typical flow rate of 10 SCFH (4.72 L/min) having 15% water by volume at a 97% saturation, the oven temperature is maintained at about 151° F. (66° C.) and a pressure of 10 psig (69 kPa gage) is maintained above each of the three stages of bubbler 26. Initially, the inlet valve 40 and outlet valve 42 of the dryer 38 are fully opened and the valve means 24 is closed. The almost fully saturated gas, forming a first mixture, thus flows from the three stage bubbler 26, through the water trap 32, the conduit 46, and the dryer 38. In passing through the dryer 38, water vapor is removed from the saturated first gas mixture forming a second mixture of dry gas. It has been found that by passing 100% of the saturated first mixture gas through the dryer 38, a minimum water vapor content of about 0.63% can be achieved, at a flow rate of 10 SCFH (4.72 L/min), by maintaining the oven temperature and bubbler pressure at the values outlined above. The second mixture of dry gas is directed, without mixing, through the mixing chamber 22 and the heated conduit 54, to the sensing head 67 of the dew point measuring instrument 66 and the emission analyzer 14. The electronic gain of the emission analyzer 14 should now be adjusted to correspond with the initial calibration reading thus negating the effect of any NO loss in the bubbler stages. Further, since the second gas mixture is substantially dry, the influence of water vapor on the analyzer reading is effectively minimized.

After adjusting the emission analyzer 14, the valve means 24 is modulated to selectively decrease the amount of the saturated first mixture gas passing through the dryer 38 and controllably direct a flow of the saturated first mixture gas directly to the mixing chamber 22. The second mixture of dry gas passing from the dryer 38 is directed through the conduit 50, into the mixing chamber 22 whereupon the preselected portions of the first and second mixtures are mixed together forming a resultant third mixture. The third mixture, having a water vapor content dependent upon the relative amounts of the first and second mixtures directed to the mixing chamber 22, passes from the mixing chamber 22, through the conditioned gas discharge conduit 54 to the sensing head 67 of the dew point measuring instrument 56, and the emission analyzer 14. The observed emission analyzer reading ($R_o$) and the dew point measurements are recorded. As given above in equation (2), the value for $R_c$ is determined by multiplying the known NO concentration of the test gas 12 by one minus the water concentration as measured by the dew point measuring instrument 56. The error (% interference) may now be calculated as given in equation (1) above.

Successive measurements are made at successively increasing water vapor levels by modulating the valve means 24 to decrease the preselected portion of the saturated first gas mixture passing through the dryer 38 of the second means (20). This step is repeated until the valve means 24 is fully open and the inlet valve 40 and outlet valve 42 are closed, thereby directing all of the saturated first mixture through the mixing chamber 22, without mixing, to the heated conduit 54, the sensing head 67, and the emission analyzer 14. It is desirable to recheck the gain adjustment of the emission analyzer 14 by repeating the step of passing all of the saturated first gas mixture through the dryer 38 and measuring the dry mixture before and after successive variably saturated third mixture measurements. Further, water condensation from the resultant third mixture is prevented by maintaining the conditioned gas discharge conduit 54 at a temperature of about 150° F. (66° C.).

After determining the error (% interference) due to the presence of water vapor for varying amounts of water in a representative exhaust gas composition, the emission analyzer 14 can now be used to measure actual engine emission gases and with the aid of a dew point measuring instrument, the correction factor, determined by the above process, can be applied to the field reading.

Other aspects, objects, and advantages of this invention can be obtained from a study of the drawings, the disclosure, and the appended claims.

We claim:

1. An apparatus (10) for producing a gas having a controlled water vapor content comprising:
   an oven (16);
   a first means (18) for adding water vapor to a gas (12) and forming a first mixture, said first means (18) being disposed within said oven (16);

a second means (20) for removing water vapor from at least a portion of said first mixture and forming a second mixture, said second means (20) being disposed within said oven (16);

a mixing chamber (22) connected to said first and second means (18,20) and being disposed within said oven (16);

valve means (24) for selectively, controllably delivering preselected amounts of said first and second mixtures to said mixing chamber (22) and forming a third resultant mixture;

a coupling member (62) spaced from the oven;

a conditioned gas discharge conduit (54) communicating said mixing chamber (22) with said coupling member (62); and, a dew point measuring instrument (66), said instrument (66) having a sensing head (67) disposed within said oven (16) in fluid communication with said conditioned gas discharge conduit (54).

2. An apparatus (10), as set forth in claim 1, wherein said first means (18) is a water bubbler (26).

3. An apparatus (10), as set forth in claim 1, wherein said second means (20) is a permeation distillation dryer (38).

4. An apparatus (10), as set forth in claim 1, wherein said conditioned gas discharge conduit (54) includes a heating means (64) for maintaining said third mixture at a temperature above its dew point temperature.

5. A method for controlling the water vapor content of a gas, comprising:

adding water vapor to an unconditioned gas (12) in an amount sufficient to raise the saturation of said gas (12) to a range of from about 95 percent to about 99 percent and forming a first mixture;

removing water vapor from a preselected portion of said first mixture and forming a preselected remaining second mixture;

mixing the preselected portions of said first and second mixtures and forming a resultant third mixture; and, maintaining said third mixture at a temperature higher than the dew point temperature of said third mixture.

6. The method, as set forth in claim 5, including heating said unconditioned gas to a temperature in a range from about 40° C. (140° F.) to about 75° C. (168° F.).

7. The method, as set forth in claim 5, wherein said first and second mixtures are each maintained at a temperature in a range from about 40° C. (140° F.) to about 75° C. (168° F.).

* * * * *